US008084495B2

(12) United States Patent
Hancke Orozco et al.

(10) Patent No.: US 8,084,495 B2
(45) Date of Patent: Dec. 27, 2011

(54) COMPOSITION OF LABDANE DITERPENES EXTRACTED FROM ANDROGRAPHIS PANICULATA, USEFUL FOR THE TREATMENT OF AUTOIMMUNE DISEASES, AND ALZHEIMER DISEASE BY ACTIVATION FOR PPR-GAMMA RECEPTORS

(75) Inventors: Juan Luis Hancke Orozco, Valdivia (CL); Rafael Agustin Burgos Aguilera, Valdivia (CL)

(73) Assignee: Herbal Powers Corporation, Bradenton, FL (US)

( * ) Notice: Subject to any disclaimer, the term of this patent is extended or adjusted under 35 U.S.C. 154(b) by 1562 days.

(21) Appl. No.: 10/516,500

(22) PCT Filed: May 21, 2004

(86) PCT No.: PCT/EP2004/005516
§ 371 (c)(1),
(2), (4) Date: Dec. 2, 2004

(87) PCT Pub. No.: WO2005/074953
PCT Pub. Date: Aug. 18, 2005

(65) Prior Publication Data
US 2006/0063831 A1    Mar. 23, 2006

(30) Foreign Application Priority Data
Feb. 3, 2004   (CL) .................................. 178-2004

(51) Int. Cl.
A61K 31/365    (2006.01)
(52) U.S. Cl. ........................................................ 514/473
(58) Field of Classification Search ............... 514/231.5, 514/269, 365, 473, 382, 367; 544/314, 152
See application file for complete search history.

(56) References Cited

U.S. PATENT DOCUMENTS

| | | | | |
|---|---|---|---|---|
| 5,833,994 A * | 11/1998 | Wheelock et al. | .......... | 424/198.1 |
| 5,883,074 A * | 3/1999 | Boggs et al. | ...................... | 514/8 |
| 6,140,063 A * | 10/2000 | Wheelock et al. | ............. | 435/7.1 |
| 6,313,269 B1 * | 11/2001 | Deen et al. | ..................... | 530/350 |
| 6,410,590 B1 * | 6/2002 | Nanduri et al. | ................. | 514/462 |
| 6,486,196 B2 * | 11/2002 | Nanduri et al. | ................. | 514/452 |
| 2002/0016324 A1 * | 2/2002 | Nanduri et al. | ............ | 514/231.5 |
| 2002/0068098 A1 * | 6/2002 | Babish et al. | ................. | 424/725 |
| 2002/0077350 A1 * | 6/2002 | Babish et al. | ................. | 514/453 |
| 2003/0108628 A1 | 6/2003 | Babish et al. | | |

FOREIGN PATENT DOCUMENTS

| WO | 9617605 | * | 6/1996 |
|---|---|---|---|
| WO | WO96/17605 A | | 6/1996 |
| WO | 9830213 | * | 7/1998 |

OTHER PUBLICATIONS

Samaha et al., "Effect of resiglitazone on lipids, adipokines, and inflammatory markers in nondiabetic patients with low high-density lipoprotein cholesterol and metabolic syndrome", Journal of the American heart association, 2006, vol. 26, pp. 624-630.*

Vasantha et al., "SIRT1 modulating compounds from high-throughput screening as anti-inflammatory and insulin-sensitizing agents", Journal of biomolecular screening, 2006, vol. 11, pp. 959-967.*
http://familydoctor.org/online/famdocen/home/common/heartdisease/basics/826.printerview, (2005).*
Saso et al., "Abnormal Glycoxylation of α-Macroglobulin, A non-acute-phase protein, in patients with autoimmune diseases", Inflammation, vol. 17, pp. 465-479, (1993).*
Onat et al., "Metabolic syndrome: major impact on coronary risk in a polulation with low cholesterol levels—a prospective and cross-sectional evaluation", Atherosclerosis, vol. 165, pp. 285-292, (2002).*
Vickers et al. "Adult growth hormone treatment reduces hypertension and obesity induced by an adverse prenatal environment", Journal of Endocrinology, vol. 175, pp. 615-623, (2002).*
Panossian et al., "Effect of Andrographolide and Kan Jang fixed combination of extract SHA-10 and extract SHE-3—on proliferation of human lymphocytes, production of cytokines and immune activation markers in the whole blood cells culture", Phytomedicine, vol. 9, pp. 598-605, (2002).*
Smith et al., "PPAR-Y receptor agonists—a review of their role in diabetic management in Trinidad and Tobago", Molecular and Cellular Biochemistry, 200, vol. 263, pp. 189-210, (2004).*
Miterski et al., "Inhibitors in the NFkB cascade comprise prime candidate genes predisposing to multiple sclerosis, especially in selected combinations", Genes and Immunity, 2002, vol. 3, pp. 211-219, (2002).*
Daly et al., "Dietary carbohydrates and insulin sensitivity: a review of the evidence and clinical implications", American Society for Clinical Nutrition, 1997, vol. 66, pp. 1072-1085, (1997).*

(Continued)

*Primary Examiner* — Janet Andres
*Assistant Examiner* — Niloofar Rahmani
(74) *Attorney, Agent, or Firm* — Pharmaceutical Patent Attorneys, LLC (57) ABSTRACT

The diterpenic labdane 3-[2-[decahydro-6-hydroxy-5-(hydroxymethyl)-5,ha-dimethyl-2-methylene-1-naphthalenyl] ethylidene]-dihydro-4-hydroxy-2(3h)-furanone, chemically diagrammed as

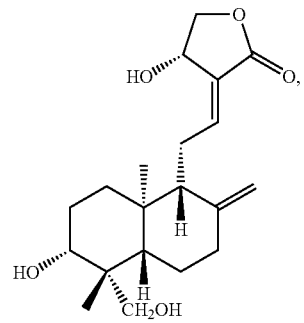

inhibits the synthesis of pro-inflammatory cytokines, activates the PPAR-gamma receptor and diminishes nuclear factor kappa B.
The compound is useful to treat auto-immune diseases, for organ and tissue transplantation, and to treat immunodeficiency (e.g., AIDS).

11 Claims, 5 Drawing Sheets

OTHER PUBLICATIONS

H.Y. Cheung et al., "Determination of Bioactive Diterpinoids from *Andrographis paniculata* by Micellar Electrokinetic Chromatography," 930 J. Chromatog. 171-76 (Sep. 28, 2001) (Elsevier Science, publ.).

S.S. Handa et al., "Hepatoprotective Activity of Andrographolide from *Andrographis paniculata* Against Carbontetrachloride," 92 Indian J. Med. Res. 276-83 (Aug. 1990) (ISSN: 0971-5916).

P.P. Gupta et al., "Antiallergic Acivity of Andrographolides Isolated from *Andrographis paniculata* (Burm. F) wall," 36 Pharma. Biol. 72-74 (Jan. 1998).

X-F. Zhang et al., "Antihyperglycemic and Anti-Oxidant Properties of *Andrographis paniculata* in Normal and Diabetic Rats," 27 Clin Exper. Pharmacol. and Physiol. (2000).

\* cited by examiner

COMPOSITION OF LABDANE DITERPENES EXTRACTED FROM ANDROGRAPHIS PANICULATA, USEFUL FOR THE TREATMENT OF AUTOIMMUNE DISEASES, AND ALZHEIMER DISEASE BY ACTIVATION FOR PPR-GAMMA RECEPTORS

RELATED APPLICATIONS

This application claims priority from Patent Cooperation Treaty Application Serial No. PCT/EP04.00515 (filed 12 May 2004) and from Chile national patent application Serial No. CL 178-2004 (filed 3 Feb. 2004), the contents of which are incorporated here by reference.

UNITED STATES GOVERNMENT INTEREST

None.

DESCRIPTION

The main objective of immunopharmacology and biopharmacy, is the continuous search of new therapeutic solutions for treating the symptoms and modify the course of immunological diseases.

BACKGROUND

Autoimmune diseases are characterized by a reaction of the immune system against its own organism. These reactions may, for example, be caused by the recognition of auto-antigens by the T lymphocytes, which trigger humoral (auto-antibodies production) and cellular (increased lymphocytes and macrophages cytotoxic activity) immune responses. Autoimmune diseases include: rheumatoid diseases, psoriasis, systemic dermatomyocytis, multiple sclerosis, lupus erythematosus, and exaggerated immune responses to antigens, i.e., asthma, allergies to drugs and food, etc. All these diseases are limiting, chronic, and in some cases lethal, and no effective therapy exists nowadays to treat them. Therefore, any drug, medicine, or media that is able to cause remission or decrease in the course of the disease, represents a significant solution for the patients health.

The search for a treatment for autoimmune diseases has resulted in an important effort to find suitable drugs and methods.

At present, the treatment of these diseases is principally based in the use of immunosuppressant drugs, such as glucocorticoids, calcineurin inhibitors, anti-proliferatives and anti-metabolites. However, since these pharmacological therapies act on many different targets, they can reduce the immune function as a whole, or due to long term use, can have the disadvantage of different cytotoxic effects and may therefore can suppress the immune system in a non specific way, exposing the patient to the risk of infections and cancer. Calcineurin and glucocorticoids exhibit an additional disadvantage, due to their nephrotoxicity and diabetogenic effects, that limits their utility in several clinical conditions (e.g., renal insufficiency, diabetes).

The latest therapeutic advances in immuno-suppression are the anti-CD3 monoclonal antibodies, the anti IL-2 receptor monoclonal antibodies, and the anti-TNF-alpha monoclonal antibodies. Despite the fact that these treatments exhibit marked immunosuppressing effects, anaphylaxis reactions, opportunistic infections (e.g., tuberculosis) and neoplasms, fever, urticaria, hypotension and dyspnea are associated with these medicines, representing a serious problem in the application of said compositions and pharmaceutical products. In injectable applications, one out of three patients can experience itching, swelling and pain.

BRIEF SUMMARY OF THE INVENTION

The present invention is able to diminish the auto-immune response (which characterizes autoimmune diseases and allergies), alleviating the symptoms and the course of these diseases, while mainting "immunological tolerance," or a healthy absence of an auto-immune response.

In other words, the composition disclosed in the present invention, may be characterized by the immunological tolerance associated with it, which immune tolerance corresponds to the active state of the absence of a specific reaction against an antigen (in other words, without causing the adverse side-effects associated with currently-used immunosuppressant drugs).

We believe that our composition inhibits the synthesis and expression of interferon gamma and interleukin-2 ("IL-2"), stimulates the PPAR gamma receptor, and reduces the in vivo activity of NF kappaB factor.

Consequently, we believe these new diterpenic labdanes selectively reduce over-expression of cytokines, which over-expression is often involved in the pathogenesis of autoimmune diseases.

Recent advances in scientific understanding of the mediators involved in acute and chronic inflammatory diseases and cancer have led to new strategies in the search for effective therapeutics. Traditional approaches include direct target intervention such as the use of specific antibodies, receptor antagonists, or enzyme inhibitors having all of them an important level of side effects (e.g. allergies, gastrointestinal ulcers, bleedings, etc.). Recent breakthroughs in the elucidation of regulatory mechanisms involved in the transcription and translation of a variety of mediators have led to increased interest in therapeutic approaches directed at the level of gene transcription (e.g. COX2, iNOS, IL1beta, TNFalpha, ICAM, etc.).

One of the most important mediators of the immune system is NF-kappaB. NF-kappa B belongs to a family of closely-related dimeric transcription factor complexes. These are each composed of various combinations of the Rel/NF-kappaB family of polypeptides. The family consists of five individual gene products in mammals, RelA (p65), NF-kappaB1 (p50/p105), NF-kappaB2 (p49/p100), c-Rel, and RelB, all of which can form hetero- or homodimers. These proteins share a highly homologous 300 amino acid "Rel homology domain" which contains the DNA binding and dimerization domains. At the extreme C-terminus of the Rel homology domain is a nuclear translocation sequence important in the transport of NF-kappaB from the cytoplasm to the nucleus. In addition, p65 and cRel possess potent trans-activation domains at their C-terminal ends.

The activity of NF-kappaB is regulated by its interaction with a member of the inhibitor IkappaB family of proteins. This interaction effectively blocks the nuclear localization sequence on the NF-kappaB proteins, thus preventing migration of the dimer to the nucleus. A wide variety of stimuli activate NF-kappaB through what are likely to be multiple signal transduction pathways. Included are bacterial products (LPS), some viruses (HIV-1, HTLV-1), inflammatory cytokines (TNFalpha, IL-1), and environmental stress. Apparently common to all stimuli however, is the phosphorylation and subsequent degradation of IkappaB IkappaB is phosphorylated on two N-terminal serines by the recently identified IkappaB kinases (IKK-alpha and IKK-beta). Site-directed mutagenesis studies indicate that these phosphorylations are critical for the subsequent activation of NF-kappaB in that once phosphorylated the protein is flagged for degradation via the ubiquitin-proteasome pathway. Free from IkappaB, the active NF-kappaB complexes are able to translocate to the nucleus where they bind in a selective manner to preferred gene-specific enhancer sequences. Included in the genes regulated by NF-kappaB are a number of cytokines, cell adhesion molecules, and acute phase proteins.

It is well-known that NF-kappaB plays a key role in the regulated expression of a large number of pro-inflammatory mediators including cytokines such as IL-6 and IL-8. Cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-kappaB in inflammatory disorders is further strengthened by studies of airway inflammation including asthma, in which NF-kappaB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NFkappaB, one may speculate that these effects are mediated through an inhibition of NFkappaB.

Further evidence for a role of NF-kappaB in inflammatory disorders comes from studies of rheumatoid synovium. Although NF-kappaB is normally present as an inactive cytoplasmic complex, recent immunohistochemical studies have indicated that NF-kappaB is present in the nuclei, and hence active, in the cells comprising rheumatoid synovium. Furthermore, NF-kappaB has been shown to be activated in human synovial cells in response to stimulation with TNF-alpha. Such a distribution may be the underlying mechanism for the increased cytokine and eicosanoid production characteristic of this tissue. See Roshak, A. K., et al., J. BIOL. CHEM., 271, 31496-31501 (1996).

Further evidence for a role of NF-kappaB in inflammatory disorders comes from studies of rheumatoid synovium. Although NF-kappaB is normally present as an inactive cytoplasmic complex, recent immunohistochemical studies have indicated that NF-kappaB is present in the nuclei, and hence active, in the cells comprising rheumatoid synovium. Furthermore, NF-kappaB has been shown to be activated in human synovial cells in response to stimulation with TNF-alpha. Such a distribution may be the underlying mechanism for the increased cytokine and eicosanoid production characteristic of this tissue. See Roshak, A. K., et al., J. Biol. Chem., 271, 31496-31501 (1996).

The NF-kappaB/Rel and IkappaB proteins are also likely to play a key role in neoplastic transformation. Family members are associated with cell transformation in vitro and in vivo as a result of over-expression, gene amplification, gene rearrangements or translocations. In addition, rearrangement and/or amplification of the genes encoding these proteins are seen in 20-25% of certain human lymphoid tumors. In addition, a role for NF-kappaB in the regulation of apoptosis has been reported strengthening the role of this transcription factor in the control of cell proliferation.

The first plant-derived modulators of NF-kB were reported nearly a decade ago by Kopp & Ghosh (1994) who identified sodium salicylate and its semi-synthetic derivative, aspirin. Following this discovery, a number of new natural products, of different chemical classes, have demonstrated NF-kB inhibitory activity.

Several NF-kappaB inhibitors are described in the literature. See e.g., C. Wahl, et al. J. Clin. Invest. 101(5), 1163-1174 (1998), R. W. Sullivan, et al. J. Med. Chem. 41, 413-419 (1998), J. W. Pierce, et al. J. Biol. Chem. 272, 21096-21103 (1997). The marine natural product hymenialdisine is known to inhibit NF-.kappa.B. Roshak, A., et al., JPET, 283, 955-961 (1997). Breton, J. J and Chabot-Fletcher, M. C., JPET, 282, 459-466 (1997). Salicylanilides are known compounds and described by M. T. Clark, R. A. Coburn. R. T. Evans, R. J. Genco, J. Med. Chem., 1986, 29, 25-29.

Recently, an important mechanism of the inhibition of NF-kappaB suggest the possible activation of the receptors for peroxysomes.

The receptors for peroxysomes known as "Peroxysomes Proliferator Activated Receptors" (PPARs), [attending to the usual use of the term expressed in its abbreviation known in the scientific area, said abbreviation shall be used for identifying this receptor] have been implicated in autoimmune diseases and other diseases, i.e diabetes mellitus, cardiovascular and gastrointestinal disease, and Alzheimer's disease. The current pharmaceutical agents with PPAR gamma agonist are still in the experimental stage and have significant side effects for human health, due to its mechanism of action. Therefore, there is the need to develop new agents with lesser toxic effects that can modulate these receptors more accurately in order to prevent, treat and/or alleviate the above mentioned diseases or conditions.

This new composition, modulates these receptors more accurately, and therefore allows preventing, treating and/or alleviating autoimmune diseases more efficiently, without causing undesirable side effects to the patients.

Peroxysomes Proliferator Activated Receptors (PPARs) are members of the nuclear hormone receptor super family, which are ligand-activated transcription factors regulating gene expression. Various subtypes of PPARs have been discovered. These include PPARalpha, PPARbeta or NUC1, PPARγ and PPARdelta.

PPARγ was characterized originally as a key regulator of adipocyte differentiation and lipid metabolism. PPARγ expression is directed by different promoters, leading to three PPARγ isoforms. It is now clear that PPARγ is also found in other cell types including fibroblasts, myocytes, breast cells, the white and red pulp of rat spleen, human bone-marrow precursors, and macrophages/monocytes. In addition, PPARγ has been shown in macrophage foam cells in atherosclerotic plaques. An important role for PPARγ in glucose metabolism was identified when it was demonstrated that a class of antidiabetic drugs, the thiazolidinediones, were high-affinity PPARγ ligands. The thiazolidinediones were developed originally for the treatment of type-2 diabetes on the basis of their ability to lower glucose levels (and levels of circulating fatty acids) in rodent models of insulin resistance. The finding that the thiazolidinediones mediate their therapeutic effects through direct interactions with PPARγ established PPARγ as a key regulator of glucose and lipid homeostasis. Despite being described initially as a regulator of lipid and glucose metabolism, PPARγ has also been demonstrated recently to have a role in cell proliferation and malignancy. Ligands for PPARγ have been shown to mediate positive and negative effects on cell proliferation and malignancy.

In addition to the thiazolidinedione class of antidiabetic drugs, a variety of nonsteroidal anti-inflammatory drugs also can function as PPARγ ligands, although the latter have relatively low affinity.

The prostaglandin $D_2$ ($PGD_2$) dehydration product $PGJ_2$ was the first endogenous ligand discovered for PPARγ. The additional $PGD_2$ dehydration product, 15-deoxy-$\Delta^{12,14}$-$PGJ_2$ (15d-$PGJ_2$), is also a naturally occurring substance that binds directly to PPARγ and is a potent ligand for PPARγ activation.

One of the earliest findings associating PPARs and macrophages was that PPARγ was highly expressed in macrophage-derived foam cells of human and murine atherosclerotic lesions. Subsequently, it has been demonstrated that PPARγ is expressed in human and murine monocytes/macrophages. Functionally, PPARγ has been shown to play a role in the differentiation and activation of monocytes and in the regulation of inflammatory activities. Many studies have demonstrated that PPARγ ligands inhibit macrophage-inflammatory responses. The anti-inflammatory effects of PPARγ activation have been demonstrated with human and murine monocyte/macrophages and monocyte/macrophage lines. Activation of macrophages normally leads to the secretion of several different proinflammatory mediators. Treatment with 15d-$PGJ_2$ or thiazolidinediones has been found to inhibit the secretion of many of these mediators (including gelatinase B, IL-6, TNF-α, and IL-1β) and also to reduce the induced expression of inducible NOS (iNOS) and the transcription of the scavenger receptor-A gene.

The relevance of PPARγ has been studied in several human autoimmune diseases and animal models of autoimmune diseases. Kawahito et al. demonstrated that synovial tissue expressed PPARγ in patients with rheumatoid arthritis (RA). PPARγ was found to be highly expressed in macrophages, and modest expression was noted in synovial-lining fibroblasts and ECs. Activation of PPARγ by 15d-$PGJ_2$ and troglitazone induced RA synoviocyte apoptosis in vitro.

It has been suggested that PPARγ is functionally relevant in freshly isolated T cells or becomes functionally relevant early in activation. In these studies, it was also demonstrated that the two ligands for PPARγ mediated inhibition of IL-2 secretion by the T-cell clones and did not inhibit IL-2-induced proliferation of such clones.

Several studies have investigated the role of PPARγ ligands in modifying animal models of autoimmune diseases. Su et al. showed that in a mouse model of inflammatory bowel disease, thiazolidinediones markedly reduced colonic inflammation. It has been proposed that this effect might be a result of a direct effect on colonic epithelial cells, which express high levels of PPARγ and can produce inflammatory cytokines. Kawahito et al. demonstrated that intraperitoneal administration of the PPAR ligands, 15d-$PGJ_2$ and troglitazone, ameliorated adjuvant-induced arthritis. Nino et al. examined the effect of a thiazolidinedione on experimental allergic encephalomyelitis and found that this treatment attenuated the inflammation and decreased the clinical symptoms in this mouse model of multiple sclerosis. Finally, Reilly et al. demonstrated that renal glomerular mesanglial cells are important modulators of the inflammatory response in lupus nephritis, secreting, when activated, inflammatory mediators including NO and cyclooxygenase products, thus perpetuating the local inflammatory response. Given the above studies, the relevance of PPARs and the utility of treatment with PPAR agonists in diseases with an inflammatory or autoimmune pathogenesis will likely continue to remain a research focus.

Recently, the issue of the specificity of 15d-$PGJ_2$ for PPARγ has been at least partially clarified. NF-κB is a critical activator of genes involved in inflammation and immunity. In this activation, the IκB kinase complex (IKK) phosphorylates the NF-κB inhibitors (IκB proteins) leading to their conjugation with ubiquitin and subsequent degradation by proteosome. This then allows freed NF-κB dimers to translocate to the nucleus and induce target genes. Rossi et al. demonstrated that the cyclopentenone PGs, including 15d-$PGJ_2$, directly inhibit and modify the IKK2 subunit of IKK. This, in turn, prevents the phosphorylation of the inhibitory IκB proteins that then target these proteins for ubiquitin conjugation and degradation. This then prevents the activation of NF-κB. Similarly, Castrillo et al. showed that in RAW 264.7 macrophage cells treated with LPS and IFN-α, incubation with 15d-$PGJ_2$ resulted in a significant inhibition of IKK2 activity and an inhibition of the degradation of the inhibitory IκB proteins. This, in turn, caused a partial inhibition of NF-κB activity and an impaired expression of genes requiring NF-κB activation, such as type-2 NOS and cyclooxygenase 2.

Therefore, it can be concluded that PPARγ and NF-?B are important mediators involved in autoimmune diseases, resulting in a stimulus to the pharmaceutical industry to search for new selective drugs and medicines that affects these mediators.

On the other hand, Alzheimer's disease (AD) is characterized by the extracellular deposition of β-amyloid fibrils within the brain and the activation of microglial cells associated with the amyloid plaque. The activated microglia subsequently secretes a diverse range of inflammatory products. Kitamura et al. assessed the occurrence of PPARγ and COX-1, COX-2, in normal and AD brains using specific antibodies and found increased expression of these moieties in AD brains. Nonsteroidal, anti-inflammatory drugs (NSAIDs) have been shown to be efficacious in reducing the incidence and risk of AD and in delaying disease progression. Combs et al. demonstrated that NSAIDs, thiazolidinediones, and $PGJ_2$, all of which are PPARγ agonists, inhibited the β-amyloid-stimulated secretion of inflammatory products by microglia and monocytes. PPARγ agonists were shown to inhibit the β-amyloid-stimulated expression of the genes for IL-6 and TNF-α and the expression of COX-2. Heneka et al. demonstrated that microinjection of LPS and IFN-α into rat cerebellum induced iNOS expression in cerebellar granule cells and subsequent cell death. Coinjection of PPARγ agonists (including troglitazone and 15d-$PGJ_2$) reduced iNOS expression and cell death, whereas coinjection of a selective COX inhibitor had no effect. Overall, work in AD seems to suggest that PPARγ agonists can modulate inflammatory responses in the brain and that NSAIDs may be helpful in AD as a result of their effect on PPARγ.

From the previously exposed herein, it can be concluded:

Till now, there are no antecedents of PPAR-γ agonist compounds isolated from medicinal plants. Nowadays, there are no drugs, compositions or medicines with these properties for the treatment of autoimmune diseases.

Whereas, this new composition is able to reduce the pro-inflammatory cytokines production, that are increased in autoimmune and neurodegenerative diseases.

Additionally, the composition of the present invention has low toxicity, and does not exhibit any harmful side effects.

Given the current "State of Art" in Science, the use of said composition cannot be deduced by an expert in the field, wherein said composition is directed for the above mentioned diseases, with said properties, maintaining the immune tolerance, without causing adverse effects, as occurs with other substances that are currently used for these diseases.

*Andrographis paniculata* (Nees), is a medicinal plant pertaining to the Acanthaceae family native to Asia, India, Malaysia, China, Korea and elsewhere. In these countries it has been widely employed for their beneficial effects of the fresh and dried plant or its components in different diseases, such as common cold, liver conditions, diabetes, etc.

DETAILED DESCRIPTION

Figure 1:
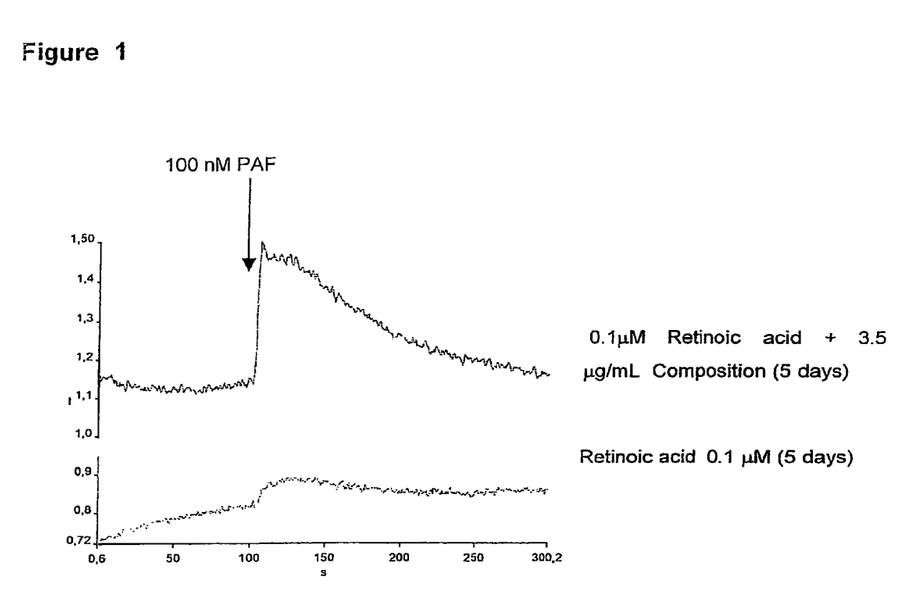
FIG. 1. Is a representative graph showing the PAF induced calcium displacement measured through the ratio 340/380 nm, using HL-60 cells marked with FURA2-AM indicator. The cells were differentiated with retinoic acid alone, or in presence with the composition of the present invention (3.5 ? g/mL), as described in examples 1-2, disclosed hereinafter.
Figure 2:
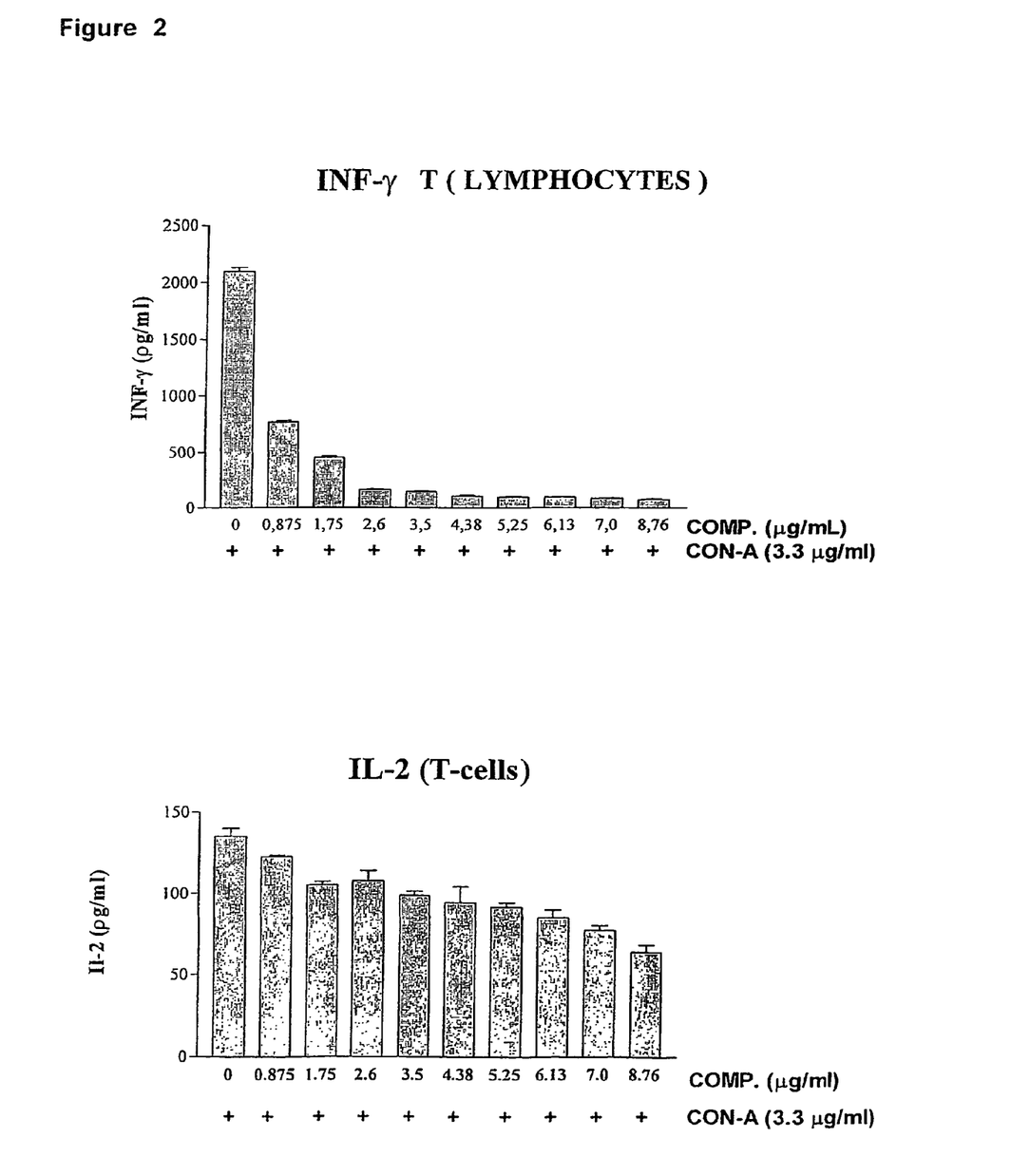
FIG. 2. Shows a bar diagram depicting the relative luciferase activity in HL-60 cells transfected with a vector that contains the promoter of PPARγ and the effect of the composition of the present invention.
Figure 3:
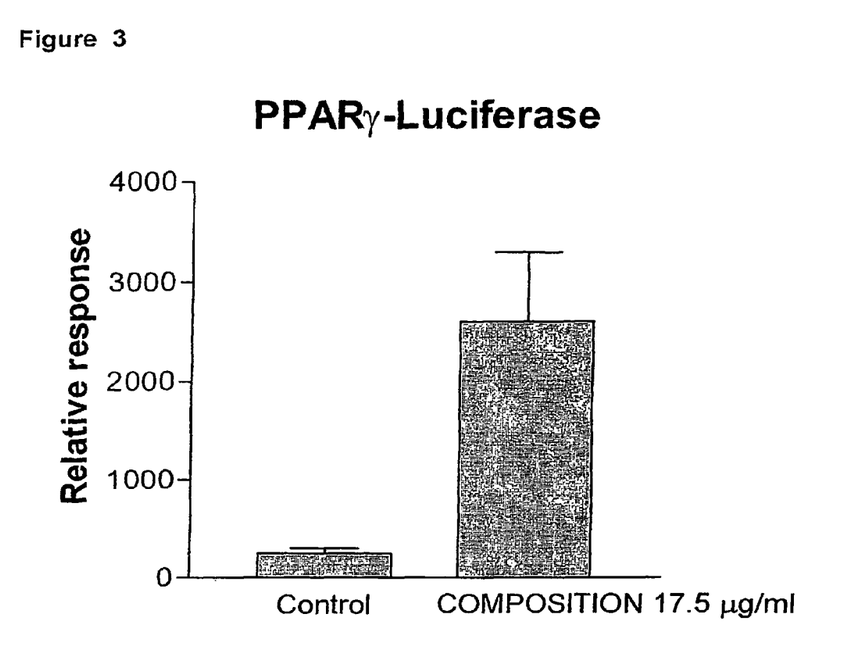
FIG. 3. Is a bar graph showing the inhibition of IL-2 and INF-gamma concentration in T cells activated with concanavalin CONA by the composition of the present invention.
Figure 4:
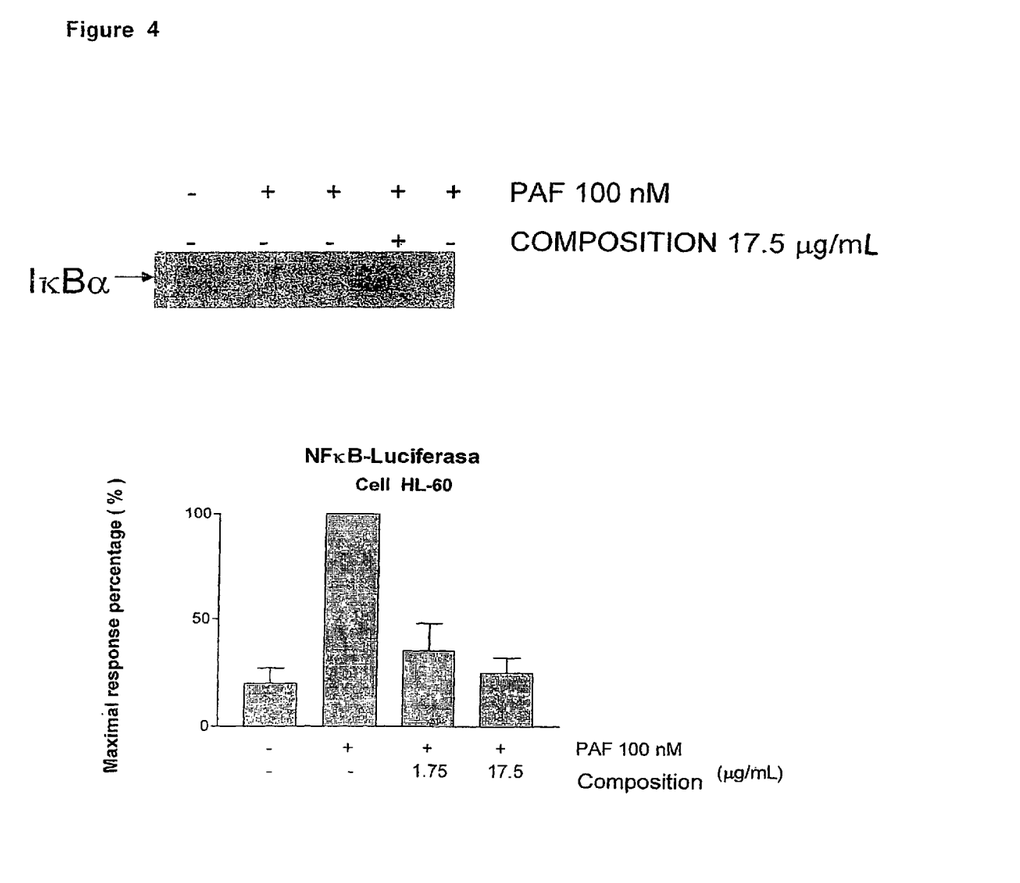
FIG. 4. Shows the inhibition of the I?Ba degradation by the composition of the present invention and the bar diagram shows the inhibition percentage of the composition of the present invention on the relative luciferase activity in HL-60 cells transfected with a vector that contains the NF? B promotor.
Figure 5:
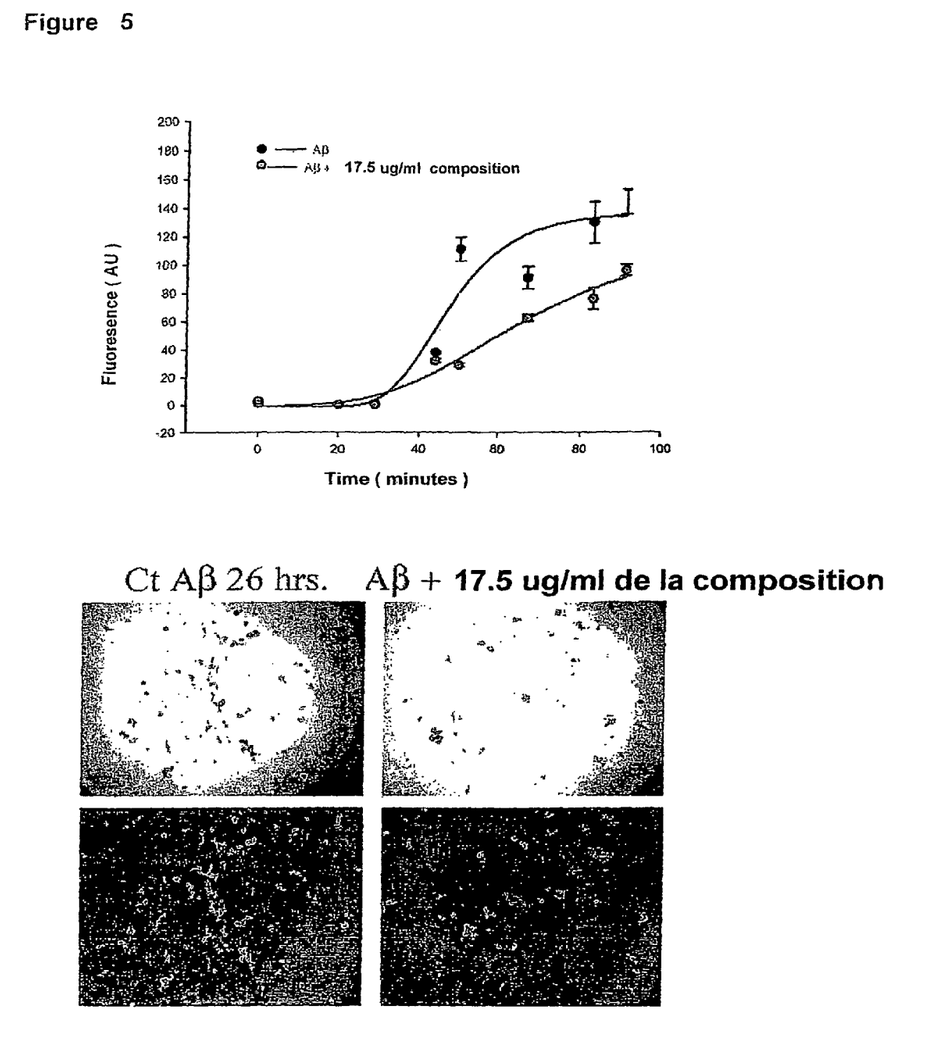
FIG. 5. Is a microphotography showing the in vitro inhibition of βamiloid formation by the composition of the present invention, using the thioflavin staining.

We have found that certain diterpenic labdanes induce PPARγ agonistic effects, and inhibit the activation of the transcription factor NF-kappaB. We sometimes call these compounds "andrographolides" because they nay be extracted from *Andrographis paniculata* (by applying the procedure disclosed herein).

The Andrographolides Composition

The composition may include a variety of diterpenic labdanes, which may be synthesized organically, or alternatively extracted from *Andrographis paniculata*. These compounds have the following general formulae:

| | |
|---|---|
| $C_{20}H_{30}O_5$ | Andrographolide |
| $C_{20}H_{30}O_4$ | 14-Deoxiandrographolide |
| $C_{26}H_{41}O_8$ | Neoandrographolide |

The chemical structure and characterization of these compounds is as follows:

Andrographolide
i. General formula: $C_{20}H_{30}O_5$
ii. Molecular weight: 350.46
iii. Molecular nomenclature: 3-[2-[decahydro-6-hydroxy-5-(hydroxy-methyl)-5,ha-dimethyl-2-methylen-1-naphtalenyl]ethylidene]di-hydro-4-hydroxy-2(3h)-furanone.

iv. Molecular structure:

14-Deoxyandrographolide
i. General formula: $C_{20}H_{30}O_4$
ii. Molecular weight: 336.46
iii. Molecular structure:

Neoandrographolide
i. General formula: $C_{20}H_{41}O_8$
ii. Molecular weight: 326.46
iii. Molecular structure:

When obtained as an extract of the plant, a typical extract includes Andrographolide, 14-Deoxyandrographolide and Neoandrographolide. The plant extract typically will contain approximately 20 to 40% w/w of Andrographolide, about 3 to 6% w/w of 14-Deoxyandrographolide, and about 0.2 to 0.8% w/w of Neoandrographolide in the dried extract. Preferably, these compounds are contained from about 25 to 35% w/w of Andrographolide, from about 4.5 to 5.5% w/w of 14-deoxyandrographolide, and approximately 0.4 to 0.8% w/w of Neoandrographolide in the final plant extract.

In a more preferred embodiment of the plant extract, the extract comprises:

| | |
|---|---|
| Andrographolide | 24.6% |
| 14-Deoxyandrographolide | 4.8% |
| Neoandrographolide | 0.6% |

For certain applications (clinical testing, for example) the various components may be isolated so that, for example, the test subject or patient is administered only one of these three compounds. These compounds are acceptable for manufacturing medicines which can be administered with a pharmaceutically acceptable carrier, i.e. a tablet form, administered in a dose comprising approximately 1 to 6.5 mg/kg BW/day of the three-component mixture.
 a) 1-5 mg Andrographolide/kg per day
 b) 0.2-1 mg 14-Deoxiandrographolide/kg per day
 c) 0.02-0.12 mg NeoAndrographolide/kg per day.

Without affecting other formulation and administration embodiments, those herein disclosed, contribute efficiently and effectively for the treatment of autoimmune diseases already mentioned and also for treating Alzheimer's disease, according to the examples disclosed herein.

Therefore, both the composition and its pharmaceutical formulation particularly when administered in the tablet form and in the above indicated doses, provide a medicine for treating a variety of autoimmune diseases such as: inflammatory disorders; particularly, diabetes mellitus, inflammatory bowel disease; autoimmune diseases (lupus erithematosus, multiple sclerosis and rheumatoid arthritis).

Due to its mechanism of action, the compounds and the pharmaceutical composition herein disclosed can also be useful for treating AIDS and tissue and organ rejection.

The pharmaceutical composition that can be manufactured with the composition of the present invention, specially according to the revealed formulation, can correspond to enteral, parenteral, dermic, ocular, nasal, otic, rectal, vaginal, urethral, bucal, pharyngeal-tracheal-bronchial pharmaceutical forms.

Method of Obtaining and Analysis of *Andrographis paniculata* Raw Material
 Active ingredient: *Andrographis paniculata* Nees (Burm. f.)
 Family: Acantaceae
 Used part: herba The green leaves, stems and higher parts, organically cultivated under supervision of the inventor including the seeds are sun dried. All foreign materials are manually removed and the raw material is cut into 1-1.5 cm size pieces, which are stored in a ventilated area. Routine analysis is carried out in order to asses the identity: macro and microscopic analysis, organoleptic parameters and TLC analysis (thin layer chromatography) is performed according to European Pharmacopoeia.

Method for Obtaining the *Andrographis paniculata* Dried Extract

The extraction of *A. paniculata* is performed by continuous percolation of the grinded dried plant (aerial part) using a polar solvent in part 1.

The duly analyzed drug material is grinded to suitable particle size in a knife-hammer mill (0.8 cm$^2$). The grinded material is charged into stainless steel percolators and the extraction solution is added at a temperature of 50° C. The percolation time is of approximately 6 days (6×24 hours) in two extraction cycles. The percolate is collected in stainless steel tanks until the percolation is completed. The percolate is transferred directly to an evaporation unit in order to eliminate the solvent and most of the water. Evaporation is performed in a LUWA thin-film evaporator at 140-158° F. (60-70° C.) and 0.65-0.85 bar vacuum. The evaporation process is performed in 3-4 cycles, where the extract is kept under mixing, 4 times during 30 minutes per day. When the spissum extract has the right content of water, the following analysis are made: ash content, HCL-ash, loss on drying, pH value, TLC identity and HPLC (high performance liquid chromatography), analysis for Andrographolide, 14-Deoxiandrographolide and Neoandrographolide. Then the spissum extract is transferred to the drying unit. Before drying, The final dried extract is packaged in plastic bags in fiber drums for subsequent analysis.

Method of Preparation of *Andrographis Paniculata* 30% Extract:

Cut and sieved leaves/stem of *Andrographis paniculata* are collected from farms under direct control of the inventors. The aerial parts are analyzed for identity as previously described and then taken for extraction.

The aerial parts are extracted in a Stainless steel extraction unit under vacuum with a low polarity solvent (A), such as N-hexane or chloroform. Following successive extractions, the solvent is removed and the marc is treated with a second solvent having higher polarity (B) such as Pet ether 40:60 or ethyl acetate, after a single extraction, the solvent is removed and the marc is treated with a solvent (C) having greater polarity such as ethanol or water.

The third solvent is recovered and evaporated leaving behind a mass with 30-40% moisture, the marc is treated with a solvent having low polarity as described previously, the mass is then filtered and dried under vacuum till there is less than 5% moisture. The granules are ground to a fine powder having not less than 30% labdane diterpenes calculated as andrographolides.

Details of Extraction:
 Step 1: Finely cut leaves/stem of *Andrographis paniculata* are loaded in an S S reactor with between 3-5 times w/w of solvent A.
 Step 2: The herb is extracted for between 4-6 hours repeatedly and the solvent removed.
 Step 3: The marc is then treated with a solvent B having higher polarity than solvent A and extracted once for 3-5 hours.
 Step 4: The solvent B is removed and the marc is then extracted with solvent C having higher polarity than solvents A or B.
 Step 5: The solvent C is circulated through the marc for 3-5 hours and removed under vacuum to an S S evaporator and the marc is again extracted with solvent C, this process is repeated 3-4 times.
 Step 6: The solvent C is recovered from all the washings and the resulting mass pooled together
 Step 7: The mass obtained from Steps 4-7 is then treated with Solvents A or B and the residue is dried under vacuum at a temperature not exceeding 60 C.
 Step 8: The dried mass that is obtained from Step 7 is powdered using a GMP Grinder having stainless steel meshing between 100-200 ASTM.
 Step 9: The powder obtained from Step 8 is sieved through an auto siever and directly filled into sterilized PP bags ready to be sealed.

The powder obtained as described above is analyzed as per the protocols described in this document having 25 to 35% w/w of Andrographolide, from about 4.5 to 5.5% w/w of 14-deoxyandrographolide, and approximately 0.4 to 0.8% w/w of Neoandrographolide in the final extract.

Identity of *Andrographis paniculata*—TLC

Test solution: To 1 g herbal extract, 20 ml of methanol is added, shaken for about 1 hour and the methanol is decanted through a filter. The residue is shaken with 20 ml methanol, filtered and mixed with the first extract (making 40 ml of test solution).

Reference solutions: 1 Andrographolide (A), 14-Deoxiandrographolide (DA) and Neoandrographolide (NA), dissolved in methanol. 2. Reference-extract treated in the same way as the test-extract. 20-30 ul test solution is applied to a TLC-plate (silica gel GF254 as coating substance) and developed over a path of 15 cm using a mixture of 77 volumes of ethyl acetate, 15 volumes of methanol and 8 volumes of water (77:15:8). Subsequently, the plate is allowed to dry in air and examined under UV (254 nM). The few dark spots of the chromatogram correspond to Andrographolide at a $R_f$: 0.65-07; 14-Deoxiandrographolide Rf: 0.75-0.8 and Neoandrographolide, $R_f$: 0.60-0.65.

HPLC Method for the Quantification of Diterpenic Labdanes

The three compounds are extracted with acetone (4:1) and then analyzed by HPLC using a reverse phase RP-C18 licrospher column (4×125 mm). The mobile phase consists of acetonitrile 26% and phosphoric acid 0.5%, at a rate of 1.1 ml/min, and is detected at 228 nm according to Burgos et al.; 1999, Acta Hort. (ISHS) 501:83-86.

The *Andrographis paniculata* dried extract is standardized to a minimum of 30% of total Andrographolides, which comprises approximately 20 to 40% w/w of andrographolide, 3 to 6% w/w of 14-deoxyandrographolide, and 0.2 to 0.8% w/w of neoandrographolide.

The composition according to the present invention has not been previously disclosed in the Current "state of the art" in science and there are no antecedents about the use of the same in order to solve the described methodological problems concerning autoimmune diseases and AD.

The pharmaceutical compositions of this invention may be administered orally or parenterally, and the parenteral administration comprises intravenous injection, subcutaneous injection, intramuscular injection and intraarticular injection.

The correct dosage of the pharmaceutical compositions of the invention will vary depending on the particular formulation, the mode of application, age, body weight and gender of the patient, diet, disease status of the patient, complementary drugs and adverse reactions. It is understood that the ordinary skilled physician will readily be able to determine and prescribe a correct dosage of this pharmaceutical compositions. Preferably, the daily dosage of this pharmaceutical compositions ranges from 1-6.5 mg of the andrographolides mixture per kg of body weight.

According to the conventional techniques known to those skilled in the art, the pharmaceutical compositions of the present invention can be formulated with a pharmaceutical acceptable carrier and/or vehicle as described above, such as a unit dosage form. Non-limiting examples of the formulations include, but are not limited to, a sterile solution, a solution, a suspension or an emulsion, an extract, an elixir, a powder, a granule, a tablet, a capsule, a liniment, a lotion and an ointment.

The present invention also embraces the pharmaceutical compositions containing Andrographolide, 14-Deoxiandrographolide and Neoandrographolide Labdanes compounds in combination with pharmaceutically acceptable carriers normally employed in preparing such compositions.

In the pharmaceutical compositions of this invention, the pharmaceutically acceptable carrier may be any conventional one described for pharmaceutical formulations, such as lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, Hydroxypropylmethylcellulose (HPMC), methylhydroxy benzoate, propylhydroxy benzoate, talc, stearic acid, magnesium and mineral oil, but not limited thereto. Additionally, the pharmaceutical compositions of the present invention may contain any of a wetting agent, sweetening agent, emulsifying agent, suspending agent, preservatives, flavors, perfumes, lubricating agent, or mixtures of these substances.

Typically, the pharmaceutical compositions contains from 20-40%, preferably from 25 to 35%, and most preferably 30% w/w of Andrographolide, 14-Deoxiandrographolide and Neoandrographolide Labdanes of the mixture, and the pharmaceutically acceptable carriers.

The pharmaceutical composition of the present invention can be administered to mammals in need thereof, via oral route administered singly or as a divided dose.

Thus, for oral administration, the compounds can be combined with a suitable solid carrier to form capsules, tablets, powders. Additionally, the pharmaceutical compositions may contain other components such as flavoring, sweeteners, excipients and the like.

Additionally, the present invention provides a method for treating patients with the composition containing the andrographolides mixtures which comprises: intravenous administering of the solution and orally administering the tablets comprising the composition of the present invention to patients in need thereof. The preferred dosage of the injection solution formulation is about 60 to 210 mg/day, most preferably, 60-80 mg/day, of the composition per day in one, two or three injections.

The present formulation in the injectable solution form comprises 8-16 mg approximately of the composition per ml. When administered to patients, the composition is preferably diluted to about 1:5 to 1:10 volume of 0.9% saline solution.

The following examples are illustrative, but do not limit the scope of the present invention. Reasonable variations, such as those occurring to a reasonable artisan, can be made herein without departing from the scope of the present invention.

The pharmaceutical composition of the present invention is suitable for preparation in a scale typical for pharmaceutical industry as well as for smaller measure. Following conventional techniques of the pharmaceutical industry involving wet granulation, dry granulation, direct compression, fluid bed granulation, when necessary, for tablet forms, as appropriate, to give the desired oral, or parenteral products.

The percentages indicated in the following examples are all given by weight.

EXAMPLES

Exemplary of a typical method for preparing a tablet containing the active agents is to first mix the active agent with a binder such as gelatin, ethyl cellulose, or the like. Wherein the mixing is suitably carried out in a standard V-blender and usually under anhydrous conditions. Next, the just prepared mixture can be slugged through conventional tablet machines and the slugs fabricated into tablets. The freshly prepared tablets are coated, with suitable coatings including shellac, methylcellulose, carnauba wax, styrene-maleic acid copolymers, and the like.

For oral administration, the compressed tablets containing from 30 mg up to 40 mg of the andrographolide mixture are manufactured according to the above disclosed methods of manufacturing techniques well known to the art and set forth in Remington's Pharmaceutical Science, Chapter 39, Mack Publishing Co., 1965.

The preferred pharmaceutical compositions of the present invention formulations are shown in some of the following Examples.

Example 1

Pharmaceutical composition for preparing a tablet of the present invention, using the andrographolide mixture contained in the dried extract obtained from the herb *Andrographis paniculata* Nees.

| Ingredients: Per tablet | mg. |
|---|---|
| Dried Extract (Andrographolides mixture) | 135.0 |
| Potato starch | 168.8 |
| Talc | 106.9 |
| Gelatin | 11.5 |
| Magnesium stearate | 5.6 |
| Hydroxypropyl methyl cellulose | 3.5 |
| Silicon dioxide, anhydrous | 2.0 |
| Polyethylene glycol | 0.7 |
| Carbonate, calcium (qsp.) | 16 |

To formulate the tablet uniformly blend the dried extract (Andrographolides mixture) active compound, potato starch, talc, gelatin, hydroxypropyl methyl cellulose, silicon dioxide, anhydrous, polyethylene glycol, and calcium carbonate under dry conditions in a conventional V-blender until all the ingredients are uniformly mixed. The mixture is then passed through a standard light mesh screen, dried in an anhydrous atmosphere and then blended with magnesium stearate, and compressed into tablets, and coated with shellac. Other tablets containing from 116 to 162 mg, are prepared in a similar fashion.

Example 2

Pharmaceutical composition for preparing a capsule of the present invention, using the dried extract obtained from the herb *Andrographis paniculata* Nees.

| Ingredients: Per capsule | mg. |
|---|---|
| Dry Extract, (Andrographolides mixture) | 135.0 |
| Potato starch | 168.8 |
| Talc | 106.9 |
| Gelatin | 11.5 |
| Magnesium stearate | 5.6 |
| Hydroxypropyl methyl cellulose | 3.5 |
| Silicon dioxide, anhydrous | 2.0 |
| Polyethylene Glycol | 0.7 |
| Carbonate, calcium | 16 |

The manufacture of capsules containing from 30 mg to 40 mg of andrographolide mixture for oral use consists essentially of mixing the dried extract, (the above-discussed three-component andrographolides mixture) with a carrier and enclosing the mixture in a polymeric sheath, usually gelatin or the like. The capsules can be in the art known soft form of a capsule made by enclosing the compound in intimate dispersion within an edible, compatible carrier, or the capsule can be a hard capsule consisting essentially of the novel composition mixed with a nontoxic solid such as talc, calcium stearate, calcium carbonate, or the like. Exemplary of a typical use is employing a capsule containing 30 mg of 40 mg.

The dose administered, whether a single dose, multiple dose, or a daily dose, will of course, vary with the particular compound of the invention employed because of the varying potency of the compound, the chosen route of administration, the size of the patient and the nature of the disease condition. The administered dose corresponds to a general oral dose of 80 to 160 mg daily, with the oral dose of normally 120 mg three times per day; the usual intravenous dose of 60 to 80 mg, followed if indicated by 70 to 100 mg at a later period, and the usual intramuscular dose of 70 to 100 mg every 24 hours, with 1 to 2 injections per day.

The novel and useful pharmaceutical compositions comprising the dried extract, (containing the above-discussed three-component mixture) of the invention are adaptable for the administration for their physiological expected effects from drug delivery systems, such as skin delivery systems, gastrointestinal drug delivery devices, and the like, wherein the delivery device is manufactured from naturally occurring and synthetic polymeric materials. Representative of materials acceptable for the fabrication of drug delivery systems containing the compounds for controlled drug administration include materials such as polyvinyl chloride, polyisoprene, polybutadiene, polyethylene, ethylene-vinyl acetate copolymers, polydimethylsiloxane, hydrophillic hydrogels of esters of acrylic and methacrylic acid, polyvinyl acetates, propylene vinyl acetate copolymers, and the like.

Example N° 3

Shellac covered tablets containing the above indicated composition are prepared following conventional techniques of the pharmaceutical industry involving mixing, granulating, and compressing, when necessary, for tablet forms.

Specifically the composition of example 1 is thoroughly mixed with a sufficient amount of *Andrographis paniculata* dried extract. For the manufacture of tablets comprising Andrographolide, 14-Deoxiandrographolide and Neoandrographolide, the mixture is compressed in a direct form with the inactive ingredients mentioned in example N° 1, and subsequently covered with shellac, accordingly.

Example N° 4

HL-60 cell differentiation induced by the composition.

Chemicals: May Grunwald-Giemsa, NBT, retinoic acid, cytochalasin B, penicillin, streptomycin, glutamine, fetal bovine serum (Sigma). RPMI 1640 (GIBCO), Fetal bovine serum from Boehringer Mannheim, all trans-retinoic acid and andrographolide was from Aldrich. The other isolates were supplied from Amsar Pvt. Ltd., India. FURA2-AM was purchased from Molecular Probes (USA). Nitroblue tetrazolium was from Sigma.

Cell Culture: HL 60 cells were grown in RPMI 1640 medium supplemented with 20% heat-inactivated fetal bovine serum, 2 mM glutamine, 100 IU/ml penicillin, and 100 pg/ml streptomycin at 37° C. in a humidified atmosphere containing 5% $CO_2$. Cells were seeded twice weekly at $3\times10^5$ cells/mil. Differentiation was induced by adding 100 nM of all-trans-retinoic acid, alone or combined with the composition (17.5 μg/ml) and assessed by the change in morphology after May Grunwald-Giemsa staining and the ability to reduce NBT' (11). Undifferentiated cultures contained less than 3% NBT positive cells. Differentiated cultures were studied after 5 days of retinoic acid treatment.

Calcium Measurement [Ca2+]c

HL-60 granulocytes ($2 \times 10^7$/ml) were loaded with 2 µM fura-2/AM in $Ca^{2+}$ medium plus 0.1% bovine serum albumin for 45 min at 37° C., then diluted to $10^7$ cells/ml and kept on ice. Just before use, 0.5 ml of this cell suspension was centrifuged and re-suspended in 2.4 ml of the indicated medium including 5 µg/ml cytochalasin B. Fura-2 fluorescence (F) was measured in a thermostated cuvette (37° C.) (LS55 fluorimeter, Perkin-Elmer Corp.) at 340 and 380 nm excitation and 505 nm emission wavelength.

Example N° 5

Inhibition of IL-2 and IFN-γ production in T cells by the composition.

Chemicals: concanavaline A and RPMI 1640 medium from Sigma.

Cell cultures: Rockefeller mice were sacrificed by ether and the popliteal ganglia and spleen were placed in a Petri plaque containing 5 ml of a medium culture RPMI 1640. The lymph cells were obtained by disrupting these organs in a RPMI 1640 sterile solution, and the lymphocytes were re-suspended in 1 ml of RPMI 1640 medium and quantified with a Neubauer chamber. Finally, the suspension of lymphocytes was adjusted to a concentration of $4 \times 10^6$ cells per ml RPMI. Once obtained, the lymphocytes were cultivated in presence or absence of the composition. For this purpose, culture plaques of poliestyrene of 24 well (2 ml each); containing 1 ml cells and different concentrations of the composition and 1 ml of the mitogen concanavaline A (CONA, 0 µg/ml and 10 µg/ml) were used.

The plaques were incubated in a oven at 37° C. in an atmosphere of humidity 5% and $CO_2$ for 24 h, then a sample of 2 ml each were added and centrifuged for one minute at 3200 rpm. Afterwards, the cells were freezed in 0.6 ml aliquots and the cytokines detected with ELISA (Enzyme Linked Immuno Sorbent Assay).

ELISA for IL-2 and IFN-γ

Chemicals: IL-2 & IFN gamma from Pharmingen; TMB from Pierce, $H_2O_2$ and $H_2SO_4$ from Merck.

For the determination of cytokines (IL-2 and IFN), a first antibody that captures the anti-antigen; a second antibody that conjugates to a peroxidase enzyme, and a standard solution for a calibration curve was used. ELISA "high binding" 96 wells polystyrene plates were used. 100 µl per well of the first antibody was diluted in carbonate buffer pH 9.5 with the aim to facilitate the sticking to the well, and incubated overnight at 4° C. to assure the binding to the solid part. Afterwards, the content of the well was eliminated and washed with 300 µl per well with Tween 20™; 0.05% p/v and PBS pH 7.0 three times. Then, the well was blocked with 200 µl of fat-free milk 5% and PBS, and incubated for 1 hour at room temperature. After completion, the content well was eliminated and washed as explained already. Then, the test samples where ridded containing the antigen, 100 µl per well in duplicate, and 100 µl of a calibration curve specific for the cytokine and incubated for 2 hours at room temperature. Afterwards, the content well was eliminated and washed 5 times according to the latter protocol. Then, the second conjugated antibody was added with the peroxidase enzyme and diluted in a PBS and SBF Solution 10%, and 100 µl was plated per well and left at room temperature during one hour. Then, washed 7 times and revealed with a TMB solution and $H_2O_2$, 100 µl per well and developed after 30 minutes in darkness, the reaction was stopped with $H_2SO_4$ 2M; 50 µl per well. The result of the reaction was measured by ELISA with a 450 ηm filter (Elx800 universal Microplate Reader, BioteK).

Example N° 6

Stimulation of PPAR-γ Receptor by the Composition

Chemicals: Dimethylsulfoxide purchased from Merck. All other reagents were purchased from PROM EGA.

Transcription Assays: HL-60 cells were transfected with pCMX-hPPARγ1, the human PPARγ1 expression vector under control of a cytomegalovirus promoter. Luciferase and β-galactosidase activities were determined; and the luciferase activity was normalized to the β-galactosidase standard in HL-60.

Plasmids: The plasmid expressing the GAL4-DNA binding domain (DBD) and the mPPARγ ligand binding domain (pGAL4 DBD-mPPARγ) was constructed by inserting the mouse PPARγ1 ligand binding domain (from amino acids 162-475), isolated as a ScaI/BamHI fragment from pGBT-mPPARγ1 in-frame into pCMXGal4 DBD.

The cells were treated with DMSO or 17.5 µg/ml composition of the present invention, and the luciferase activity was measured by chemiluminescence.

Example N° 7

NF-?B Inhibition in Neutrophyls by the Composition

Chemicals: dimethylsulfoxide (DMSO) from Merck; bovine fetal serum and RPMI-1640 medium from Gibco, USA; nitro tetrazolium blue from Sigma, pRL-TK, pGL3 and Dual-Luciferase Reporter Assay System (Promega); Fugene6 from Roche;

Cell Culture

A cellular myeloid HL-60 line from acute myeloid leukemia was used. This cells can differentiate in the presence of dimethylsulfoxide 1.3% (DMSO) (Santos-Beneit et al., 2000). The cells are kept in RPMI-1640 medium supplemented with 2 mM L-glutamine, 10% of bovine fetal serum inactivated by temperature and antibiotics with 5% $CO_2$ at 37° C. The cells are differentiated to neutrophils by incubating the neutrophyls with 1.3% of DMSO for 4 days. The differentiated cells are analyzed with nitro tetrazolium blue (NBT).

Transfection of the NFkB-pGL3 vector in HL-60 cells and luciferase measurement HL-60 cells were cultivated and differentiated to neutrophyls for 4 days, as described elsewhere. At day 4, the cells were transfected with the pGL3-NFkB vectors and as an internal control of the transfection a pRL-TK (Promega) vector was used, which is an expression vector containing a thymidine kinase promoter of herpes simplex virus, which allows the expression of moderate levels of *Renilla* luciferase. These vectors are transfected to cells by a system based on liposomes (Fugene6, Roche). Once the transfection is done, the cells are kept for 24 h, and then stimulated by PAF or FMLP at different times, in presence or absence of the composition of the present invention. Then, cellular extracts are kept at −70° C. till the measurement of the activity of luciferase. The activity of luciferase is measured by chemiluminescence, with the commercial system Dual-Luciferase Reporter Assay System (Promega) that possesses the substrates of the enzymes firefly (pGL3) and *Renilla* (pRL) luciferase.

IκBα Immunoblot

Chemicals: fMLP; PMSF and PAF were purchased from Calbiochem. Tris, NaCl, NP-40, deoxicholate, sodium dodecylsulphate, iprotease inhibitors, mercaptoethanol from Merck.

The neutrophyls were preincubated for 10 minutes, and then stimulated with fMLP (0.1 uM) and PAF (0.1 µM) for 60 min. For the analysis of proteins, the cells were lysed in a lysis tampon (50 mM Tris, pH 8.0, 150 mM NaCl, 1% NP-40, 0.5% deoxicholate, 0.1% sodium dodecylsulphate, 1 mM $Na_2VO_4$, 1 mM PMSF and 10 µg/ml de iprotease inhibitors). The proteins were quantified by the Bradford method, resolved by electrophoresis in polyacrylamide gel in denaturized conditions (SDS/PAGE) 12%, and electro transferred to a nitrocellulose membrane. The membrane was incubated with anti-IkBα antibodies, followed by a secondary peroxidase conjugated antibody and finally visualized with chemiluminescence (ECL). As a control of the quantity of proteins in the gel, the antibodies were treated with stripping solution (100 mM 2-mercaptoetanol, 2% SDS, 62.5 mM Tris-HCl, pH 6.7) and incubated with an anti-actin antibody. Finally, a densitometric analysis with the obtained signals for each antibody was performed.

Example N° 8

Inhibition of β-Amyloid Formation by the Composition in Wild Type Rats

Amyloid Formation

To check the amyloid formation two complementary techniques, thioflavine-T fluorescence (Levine, 1993; Soto et al., 1995; Reyes et al., 1997, Inestrosa et al., 2000) and Congo red binding (Alvarez et al., 1998) were used. Briefly, the assay of thioflavin-T is based on fluorescence emission of thioflavin when it binds to amyloid fibrils, showing an increasing of emission at 482 nm when it is excited at 450 nm. The Congo red assay is a very specific quantification assay to determine the amount of amyloid formed. These techniques are currently used to verify the specific amyloid formation.

Example 9

Description of a Compound Containing each of the Three Above-Discussed Andrographolides A representative composition of the present invention is a pharmaceutical formulation in tablets, which supplies the following mixture of compounds:

| | |
|---|---|
| Andrographolide | 24.6% |
| 14-Deoxyandrographolide | 4.8% |
| Neoandrographolide | 0.6% | for the subsequent manufacture of the different pharmaceutical forms, and applied in the following doses:
a) 1-5 mg andrographolide/kg per day
b) 0.2-1 mg 14-Deoxiandrographolide/kg per day
c) 0.02-0.12 mg neoandrographolide/kg per day.

Example N° 10

Clinical Efficacy of an Oral Formulation for the Treatment of Lupus Erythematous Using the mixture of andrographolides described in Example 9, a normalization of the symptoms due to lupus occurs following 3 months of administration. In addition, the composition does not interfere with the normal rebuilding effects of other traditional non-steroidal anti-inflammatory agents.

Example N° 11

Clinical Efficacy of an Oral Formulation for the Treatment of Multiple Sclerosis Using the mixture of andrographolides described in Example 9, normalization in the symptoms of the disease occurs following 3 months of treatment of the composition of the present invention. In addition, the composition does not interfere with other treatments.

Example N° 12

Clinical Efficacy of an Oral Formulation for the Treatment of Arthrosis and Rheumatoid Arthritis Using the mixture of andrographolides described in Example 9, normalization of joint stiffness due to osteoarthritis occurs following 3 months, in the presence or absence of glucosamine or chrondoitin sulphate or other anti-inflammatory drugs. In addition, the composition does not interfere with the normal joint rebuilding effects of these two proteoglycan constituents, unlike traditional non-steroidal anti-inflammatory Example N° 13

Clinical Efficacy of an Oral Formulation for the Treatment of Diabetes Mellitus

Using the mixture of andrographolides described in Example 9, normalization in the sugar levels occurs following five weeks. In addition, the composition does not interfere with the normal rebuilding effects of other sugar reducing agents.

Example N° 14

Clinical Efficacy of an Oral Formulation for Treating AIDS

An oral formulation as described in Example 9 is administered to patients who are HIV positive. Normal CD4 count is restored within 3 months of treatment.

Example N° 15

Clinical Efficacy of an Oral Formulation for Treating Alzheimer's Disease

An oral formulation as described in Example 9 is administered to patients who have manifested an early stage of Alzheimer's Disease (AD), as diagnosed by their practitioner and confirmed by an independent board-certified neurologist. Two weeks before the clinical trial, the patients undergo appropriate psychoneurological tests, such as the Mini Mental Status Exam (MMSE), the Alzheimer Disease Assessment Scale (ADAS), the Boston Naming Test (BNT), and the Token Test (TT).

Neuropsychological tests are repeated on Day 0, 6 weeks and 3 months of the clinical trial. The tests are performed by neuropsychologists who are not aware of the patient's treatment regimen.

Patients are randomly assigned to the test formulation or placebo at the start of the study. The test formulation and placebo are taken orally one or two times per day. Treatment for conditions such as diabetes, hypertension, etc. is allowed during the study. Scores are statistically compared between the test formulation and the placebo for each of the three observational periods. Without treatment, the natural course of AD is a significant deterioration in the test scores during the course of the clinical trial. Patients treated with the composition as described in the formulation are considered improved if the patients' scores remain the same or improve during the course of the clinical trial.

The patients shall receive randomly the composition or a placebo at the beginning of the study. The composition and placebo are administered twice a day. During the study the patients are allowed to be treated for conditions as diabetes, hypertension, etc. . . . The composition and placebo results are statistically compared for all the study periods. Patients using placebo show a significant cognitive deterioration. The patients treated with the composition ameliorate in a considerable way the test scores.

From the foregoing description, it is obvious that one of ordinary skill in the art may easily ascertain the essential characteristics of the present invention, and without departing from the spirit and scope thereof, make various changes and/or modifications to oure invention for adapting it to various usages and conditions. For example, 3-[2-[decahydro-6-hydroxy-5-(hydroxy-methyl)-5,ha-dimethyl-2-methylen-1-naphthalenyl]ethylidene]di-hydro-4-hydroxy-2(3h)-furanone may be synthesized using conventional organic chemical synthesis techniques, rather than being extracted from a plant source.

As such, these changes and modifications are properly, equitably and intended to be, within the full range of equivalence of the following claims. For example, one may prepare 3-[2-[decahydro-6-hydroxy-5-(hydroxy-methyl)-5,ha-dimethyl-2-methylen-1-naphthalenyl]ethylidene]di-hydro-4-hydroxy-2(3h)-furanone analogs which, while structurally different, nonetheless retain clinical efficacy for the claimed functions. We intend such analogs to be covered by the appended claims as legal equivalents of 3-[2-[decahydro-6-hydroxy-5-(hydroxy-methyl)-5,ha-dimethyl-2-methylen-1-naphthalenyl]ethylidene]di-hydro-4-hydroxy-2(3h)-furanone.

In the claims, we intend the singular to encompass at least one: thus, for example, the phrase "a compound selected from the group consisting of: A, B and C" means at least one of the three listed compounds, and possibly more than one.

The invention claimed is:

1. A method comprising:
   i) diagnosing in a patient a disease selected from the group consisting of: rheumatoid arthritis; lupus exanthematous; multipe sclerosis; asthma; allergic reation; systemic dermatomyocytis; psoriasis; osteoarthritis; and diabetes mellitus; and
   ii) administering to said patient 3-[2-[decahydro-6-hydroxy-5-(hydroxymethyl)-5,8a-dimethyl-2-methylene-1-naphthalenyl]ethylidene]-dihydro-4-hydroxy-2(3h)-furanone in an amount effective to combat said disease.

2. The method of claim 1, wherein said autoimmune disease comprises rheumatoid arthritis.

3. The method of claim 1, wherein said autoimmune disease comprises lupus exanthematous.

4. The method of claim 1, wherein said autoimmune disease comprises multiple sclerosis.

5. The method of claim 1, wherein said autoimmune disease comprises asthma.

6. The method of claim 1, wherein said autoimmune disease comprises allergic reaction.

7. The method of claim 1, wherein said autoimmune disease comprises a condition selected from: systemic dermatomyocytis; and psoriasis.

8. The method of claim 1, wherein said autoimmune disease comprises osteoarthritis.

9. The method of claim 1, wherein said autoimmune disease comprises diabetes mellitus.

10. The method of claim 1, wherein said an amount effective to combat said disease comprises from about 1 mg to about 5 mg of 3-[2-[decahydro-6-hydroxy-5-(hydroxymethyl)-5,8a-dimethyl-2-methylene-1-naphthalenyl]ethylidene]-dihydro-4-hydroxy-2(3h)-furanone per day, per kilogram of patient body weight.

11. A method comprising:
   i) identifying in a person the possible presence of Syndrome X, and
   ii) administering to said person a substance selected from the group consisting of: *Andrographis paniculata*; and an *Andrographis paniculata* extract containing 3-[2-[decahydro-6-hydroxy-5-(hydroxymethyl)-5,8a-dimethyl-2-methylene-1-naphthalenyl]ethylidene]-dihydro-4-hydroxy-2(3h)-furanone; said substance administered in an amount effective to combat Syndrome X.

* * * * *